United States Patent [19]

Palmaer

[11] Patent Number: 4,831,665
[45] Date of Patent: May 23, 1989

[54] PROTECTIVE FACE VISOR OF A FILAMENT MESH

[75] Inventor: Leif Palmaer, Värnamo, Sweden

[73] Assignee: Anderzon Invest AB, Sweden

[21] Appl. No.: 62,712

[22] Filed: Jun. 15, 1987

[30] Foreign Application Priority Data

Jul. 3, 1986 [SE] Sweden .................. 8602956

[51] Int. Cl.⁴ .............................................. A61F 9/00
[52] U.S. Cl. .................................................. 2/9; 2/433
[58] Field of Search ............... 2/9, 15, 410, 424, 426, 2/433; 210/499; 428/596, 544, 605, 224, 225; 245/8

[56] References Cited

U.S. PATENT DOCUMENTS

| 302,048 | 7/1884 | Stockley | 2/410 |
|---|---|---|---|
| 599,686 | 3/1898 | Conlisk | 2/9 |
| 766,426 | 8/1904 | Comstock | 2/4 |
| 1,004,507 | 9/1911 | Walz | 2/4 |
| 1,075,906 | 10/1913 | Duncan | 2/424 |
| 1,184,785 | 5/1916 | Stern | 2/424 |
| 1,265,764 | 5/1918 | Ferrara | 2/9 |
| 1,838,611 | 12/1931 | Bowers | 2/9 |
| 1,872,877 | 8/1932 | Bowers | 2/424 |
| 1,920,695 | 8/1933 | Brown et al. | 245/8 |
| 2,432,311 | 12/1947 | Hall | 2/424 |
| 2,801,420 | 8/1957 | Malcom | 2/9 |
| 2,824,308 | 2/1958 | Duncan | 2/433 |
| 2,909,782 | 10/1959 | Mizek | 2/9 |
| 3,030,628 | 4/1962 | Crosson | 2/433 |
| 3,169,111 | 2/1965 | Rose et al. | 210/499 |
| 4,547,908 | 10/1985 | Karlsson et al. | 2/424 |

FOREIGN PATENT DOCUMENTS 2826636  1/1979  Fed. Rep. of Germany .......... 2/424

Primary Examiner—John J. Zimmerman
Attorney, Agent, or Firm—Ostrolenk, Faber, Gerb & Soffen

[57] ABSTRACT

A protective face visor which prevents solid particles, such as wood or metal shavings, from passing through the visor and contacting the wearer's face. The visor is constructed of filaments of wire or plastic. The spacing between the filaments of the mesh, that is the dimension of an opening in the mesh, is somewhat less than the minimum dimension of the particles in one direction across the visor and substantially exceeds the minimum dimension of the particles in at least one other direction across the visor.

12 Claims, 1 Drawing Sheet

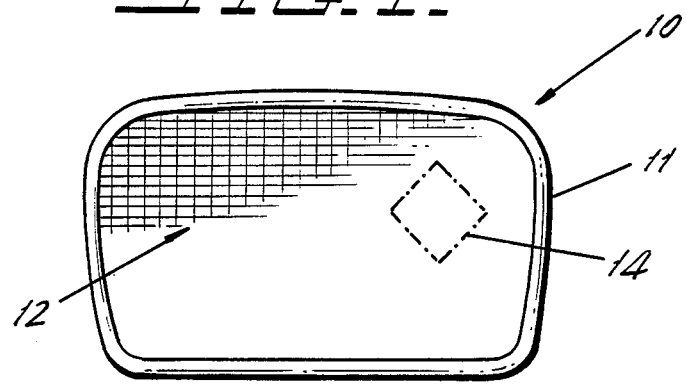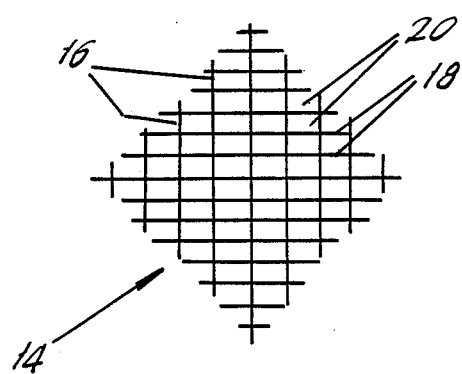

PROTECTIVE FACE VISOR OF A FILAMENT MESH

BACKGROUND OF THE INVENTION

The invention relates to a protective face visor comprised of a filament mesh, such as a mesh of wires, like metal wires, or of plastic filaments. Its preferable application is in preventing shavings produced during power-sawing from flying into the oprator's face.

Various protective means are used during forestry work in order to prevent injury. These include various types of protective face visors which are used to prevent shavings that are produced during power-sawing from flying into the operator's face, particularly in the region of his eyes. Such visors are generally hinged to the operator's helmet.

Unbroken transparent plastic visors have been tried for this purpose. Such a visor allows good visibility while preventing any solid particles from passing through. However, an unbroken visor has proven not to be a particularly good solution since resin from the shavings adheres to the visor, refraction errors may occur since a film of water easily develops in rainy weather, and the air circulation inside the visor is unsatisfactory, which causes condensation to form on the inner surface and thus considerably deteriorates the operator's vision. The poor ventilation also causes the operator's face to be insufficiently cooled. In view of these and other deficiencies, plastic visors of this type have not enjoyed great success.

A visor produced from a fine mesh or net of filaments, such as metal wire or plstic material filaments, overcomes the drawbacks mentioned above to a great extent. Such a visor is light in weight and provides good ventilation and cooling, thus eliminating any disturbing condensation. However, a traditional mesh visor has one great drawback, namely its relatively low capacity for allowing light to pass through, since the mesh must be sufficiently fine as to not allow through too many shavings particles. Despite other favorable features, there has been a certain unwillingness to utilize such visors, mainly due to the deteriorated vision of the operator. Studies that have been undertaken indicate that less than half the forest laborers who have access to such visors wear them when using a power saw.

SUMMARY OF THE INVENTION

The object of the invention is to provide a protective face visor of a filament mesh, which exhibits considerably better optical properties when traditional mesh visors, while retaining substantially equivalent ability to prevent solid particles flung against the visor from penetrating it.

This object is achieved according to the invention substantially by forming the mesh so that the spacing between the filaments of the mesh, that is the dimension of each opening in the mesh, is somewhat less than the minimum dimension of the particles or shavings in one direction and substantially exceeds that minimum dimension in at least one other direction. The openings in the mesh are preferably substantially rectangular in shape.

Other objects and features of the invention will become apparent from the following description of a preferred embodiment taken in conjunction with the accompanying drawings.

BRIEF DESCRIPTION OF THE DRAWINGS

FIG. 1 is a front view of a protective face visor according to the invention; and FIG. 2 is an enlargement of a section of the visor shown in FIG. 1 illustrating an embodiment of the visor mesh.

DESCRIPTION OF THE PREFERRED EMBODIMENT

A preferred embodiment of a visor according to the invention is shown in the drawings. The visor 10 is intended to be worn over the face of a person who is performing some operation, such as sawing wood, which is likely to generate particles of a size which could injure the person's eyes or face if any of the particles struck him. The visor includes a rigid surrounding frame 11. In known manner, the frame 11 may be hinged to or fixedly attached to a helmet or hat or may be strapped on a head band or frame worn on the head.

Stretched tautly across the frame 11 and firmly supported by it is a mesh of filaments which may be metal wire, suitable plastic or polymer material, or any other material of sufficient strength and nonstretchability that the mesh will retain its shape, the mesh filaments will not sag or stretch and the mesh filaments will not tear or move apart in normal use and when they are struck by the particles. The illustrated mesh can be more clearly seen in FIG. 2 which is an enlargement of the randomly selected section 14 of wire mesh 12. The illustrated mesh includes vertical filaments 16 and intersecting horizontal filaments 18 which cross to define rectangular shaped openings 20. The filaments may be joined at each intersection or may be conventionally woven, that is each horizontal filament 16 passes over and under alternate vertical filaments 18 and vice versa.

The significant feature of this invention lies in the shape and dimensions of the openings 20 in the mesh, which are of course established by the selected positions of the filaments 16 and 18 across the visor frame 11. In one direction, here the vertical direction along the filaments 16, the spacing between the filaments 18 of the mesh is selected to be somewhat less than the minimum dimension of the particles (not shown) which it is intended that the mesh 12 will block. In another direction, here the perpendicular, horizontal direction along the filaments 18, or perhaps along a diagonal across an opening 20, the spacing between the filaments 16, or perhaps between two opposite corners of an opening, is selected to substantially exceed the minimum dimension of the same particles. By so dimensioning the openings 20 by appropriate placement of the filaments of the mesh in the frame 11, the objectives of the invention are achieved and the below described benefits are also obtained.

In the drawings, the filaments are arranged in the frame 11 to define a mesh with rectangular shape openings 20. By simply changing the direction of extension of either of the filaments 16 or 18 across the frame 11, any other four-sided polygonal shape may be imparted to the openings 20. By adding another set of filaments or wires extending in a third direction, diagonally in FIGS. 1 and 2, for example, still other polygonal shapes may be created for the openings in the mesh. Further, a particular mesh may be created with oval shaped openings, etc. The particul ar shape of the openings in the wire or filament mesh is a matter of choice and convenience so long as the dimensional requirements of the mesh discussed above are satisfied.

In the illustrated rectangular openings, where the two directions are along the filaments 16 and 18, the ratio between the length of the short side 16 and the long side 18 of each opening 20 is a matter of choice depending upon the particular particles whose passage is to be prevented. It has been found that the benefits of the invention described herein are obtained where the ratio of the length of the short dimension of each opening to the long dimension of that opening is in the range of 0.4–0.85. A preferred ratio between the short and long sides of the opening in a rectangular mesh has been found to be 0.72.

The design of the visor proposed according to the invention offers the following advantages over traditional mesh visors formed of generally square meshes. Over the same mesh area, the light permeability of the traditional and inventive visors will be at least approximately the same, while a visor with, for instance, rectangular meshes will allow through considerably fewer particles, such as shavings, than a visor with square meshes. Furthermore, if water falls on a wire mesh visor, a film of liquid will likely form in the mesh openings due to the surface tension, thus reducing the optical properties of the visor. The likelihood of such liquid films forming in visors constructed with rectangular meshes is far less than with square meshes. Rectangular meshes "release" the water better and thus offer considerably better vision in rainy weather.

A comparison between a visor constructed from a rectangular mesh and one from a square mesh, in which the sides of the square are the same length as the short side of the rectangular, shows that the rectangular mesh visor allows through considerably more light than the square mesh one. However, both visors have substantially the same ability to deter passage of solid particles.

It has also surprisingly been found that the stability of the mesh increases with a rectangular-shaped mesh as compared with a square mesh having a square side that is of the approximate length of the short side of the rectangle. As a result, the wire diameter can be reduced, while still retaining sufficient visor stiffness.

Various types of visors have been compared in practical experiments with the visor according to the invention, with respect to light permeability and shavings penetration. A light source of specified strength has shone on the various meshes and the quantity of incident light allowed through was measured. The followed results were obtained:

|  | Mesh size in mm. | Wire diam. in mm. | Light Reduction |
| --- | --- | --- | --- |
| Polyester or polyamide net (square meshes) | 1 × 1 | 0.3 | 45% |
| Steel wire (square meshes) | 1.8 × 1.8 | 0.3 | 31% |
| Steel wire (rectangular meshes) | 1.8 × 2.5 | 0.2 | 20.5% |

Thus, with square meshes 31% of the incident light supplied was absorbed, whereas with rectangular meshes only 20.5% of the incident light was absorbed. The rectangular mesh thus absorbed 37% less light than the square mesh. Furthermore, no measurable differences could be found in the amount of shavings allowed through.

The visor according to the invention thus has vastly superior optical qualities, which should increase operator willingness to use a protective visor while working. This assumption was confirmed in a practical investigation. A group of operators selected at random was provided with protective visors of a traditional type, while a second group of the same size, also selected at random, was equipped with visors according to the invention. It was found that only about 40% of the workers in the first group used their protective visors continuously, whereas the number in the second group was about 80%.

Although the present invention has been described in connection with a preferred embodiment thereof, many variations will now become apparent to those skilled in the art. It is preferred, therefore, that the present invention be limited not by the specific disclosure herein, but only by the appended claims.

What is claimed is:

1. A protective face visor for preventing particles having a usual minimum dimension from passing through the visor, the visor comprising a mesh of filaments, including filaments extending in two different directions across the visor for defining a mesh of openings through the visor, wherein the filaments are spaced apart such that each opening in the mesh has a dimension in one direction that is less than the minimum dimension of the particles and has a dimension in at least one other direction that substantially exceeds the minimum dimension of the particles.

2. The visor of claim 1, wherein the filament mesh is comprised of a first group of filaments extending across the visor in one direction and a second group of filaments, intersecting the first group of filaments, and extending in a second direction.

3. The visor of claim 2, wherein the first and second groups of filaments intersect so that the openings in the mesh are rectangular in shape.

4. The visor of claim 1, wherein the filaments are comprised of metal wire.

5. The visor of claim 4, wherein the filaments are comprised of steel wire.

6. The visor of claim 1, wherein the filaments are comprised of a plastic material.

7. The visor of claim 6, wherein the filaments are comprised of a polymer material.

8. The visor of claim 1, wherein the filaments are comprised of a material which is generally nonstretchable and the filaments are supported in the visor for extending tautly across the visor to define the mesh.

9. The visor of claim 8, further comprising a frame around the filaments for supporting the filaments in the visor.

10. The visor of claim 1, wherein the ratio between the length dimension of the opening in the mesh in one direction and the length dimension of the opening in the mesh in the other direction is in the range of 0.4–0.85.

11. The visor of claim 2, wherein the ratio between the length dimension of the opening in the mesh in one direction and the length dimension of the opening in the mesh in the other direction is in the range of 0.4–0.85.

12. The visor of claim 3, wherein the ratio between the length dimension of the opening in the mesh in one direction and the length dimension of an opening in the mesh in the other direction is approximately 0.72.

* * * * *